(12) United States Patent
Brink et al.

(10) Patent No.: US 10,660,699 B2
(45) Date of Patent: May 26, 2020

(54) ABLATION THERAPY TO DISRUPT COORDINATED BLADDER CONTRACTIONS

(71) Applicant: Medtronic, Inc., Minneapolis, MN (US)

(72) Inventors: Thaddeus S. Brink, St. Paul, MN (US); Blake A. Hedstrom, Minneapolis, MN (US); Dwight E. Nelson, Shoreview, MN (US); Ashish Singal, Blaine, MN (US); Xin Su, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 1064 days.

(21) Appl. No.: 14/928,464

(22) Filed: Oct. 30, 2015

(65) Prior Publication Data

US 2016/0120598 A1   May 5, 2016

Related U.S. Application Data

(60) Provisional application No. 62/073,647, filed on Oct. 31, 2014.

(51) Int. Cl.
*A61B 18/14* (2006.01)
*A61B 5/20* (2006.01)
(Continued)

(52) U.S. Cl.
CPC ...... *A61B 18/1492* (2013.01); *A61B 5/04882* (2013.01); *A61B 5/1107* (2013.01);
(Continued)

(58) Field of Classification Search
CPC ......... A61B 18/02; A61B 18/06; A61B 18/10; A61B 18/12; A61B 18/1266; A61B 18/14; A61B 18/1442; A61B 18/144; A61B 18/1448; A61B 18/1482; A61B 18/1485; A61B 18/1492; A61B 2018/00517; A61B 2018/00577; A61B 2018/00642;
(Continued)

(56) References Cited

U.S. PATENT DOCUMENTS

2015/0164401 A1* 6/2015 Toth ................... A61B 5/04882
600/301

OTHER PUBLICATIONS

Fraser et al., "Bladder filling is an active process from base to dome," Society for Neuroscience, Dept. of Surgery, Duke University Medical Center, Nov. 2010, pp. 1 (Abstract Only).

(Continued)

*Primary Examiner* — Michael F Peffley
*Assistant Examiner* — Khadijeh A Vahdat
(74) *Attorney, Agent, or Firm* — Shumaker & Sieffert, P.A.

(57) ABSTRACT

The disclosure describes devices, systems, and techniques for identifying and treating bladder dysfunction. In one example, a method includes identifying one or more focal points at respective locations of bladder tissue of a bladder of a patient, the one or more focal points initiating coordinated contractions of a detrusor muscle. The method may also, or alternatively, include ablating, for each of the one or more focal points, a respective portion of the bladder tissue at the respective location of the focal point. Ablation of these targeted portions of the bladder tissue may reduce the coordinated contractions of the detrusor muscle and alleviate overactive bladder symptoms.

18 Claims, 8 Drawing Sheets

(51) Int. Cl.
*A61B 5/0488* (2006.01)
*A61B 8/08* (2006.01)
*A61B 5/11* (2006.01)
*A61B 18/00* (2006.01)
*A61B 18/08* (2006.01)
*A61B 18/06* (2006.01)
*A61B 18/02* (2006.01)
*A61B 5/00* (2006.01)

(52) U.S. Cl.
CPC ............... *A61B 5/202* (2013.01); *A61B 8/08* (2013.01); *A61B 18/1482* (2013.01); *A61B 18/1485* (2013.01); *A61B 5/6858* (2013.01); *A61B 18/02* (2013.01); *A61B 18/06* (2013.01); *A61B 18/08* (2013.01); *A61B 2018/00517* (2013.01); *A61B 2018/00577* (2013.01); *A61B 2018/00642* (2013.01); *A61B 2018/00678* (2013.01); *A61B 2018/00708* (2013.01); *A61B 2018/00815* (2013.01); *A61B 2018/00821* (2013.01); *A61B 2018/00875* (2013.01); *A61B 2018/00898* (2013.01); *A61B 2018/00982* (2013.01)

(58) Field of Classification Search
CPC  A61B 2018/00678; A61B 2018/00708; A61B 2018/00815; A61B 2018/00821; A61B 2018/00875; A61B 2018/00898; A61B 2018/00982; A61B 5/04882; A61B 5/1107; A61B 5/202; A61B 5/6858; A61B 8/08
USPC .................................................... 606/21–50
See application file for complete search history.

(56) References Cited

OTHER PUBLICATIONS

McCarthy et al., "Spontaneous Contractions Evoke Afferent Nerve Firing in Mouse Bladders With Detrusor Overactivity," Departments of Medicine, Anesthesiology and Pharmacology, University of Pittsburgh, Jan. 20, 2009, 8 pp.

* cited by examiner

ABLATION THERAPY TO DISRUPT COORDINATED BLADDER CONTRACTIONS

This application claims priority to U.S. Provisional Patent Application No. 62/073,647, filed on Oct. 31, 2014, and entitled "ABLATION THERAPY TO DISRUPT COORDINATED BLADDER CONTRACTIONS," the entire contents of which is incorporated herein by reference.

TECHNICAL FIELD

The disclosure relates to medical therapies and, more particularly, therapy for treating bladder dysfunction.

BACKGROUND

Bladder dysfunction, such as overactive bladder, urgency, or urinary incontinence, are problems that may afflict people of all ages, genders, and races. Various muscles, nerves, organs and conduits within the pelvic floor cooperate to collect, store and release urine. A variety of disorders may compromise urinary function, and contribute to an overactive bladder, urgency, and/or urinary incontinence. Many of the disorders may be associated with aging, injury or illness.

Urinary incontinence may include urge incontinence and stress incontinence. In some examples, urge incontinence may be caused by disorders of peripheral or central nervous systems that control bladder micturition reflexes. Some patients may also suffer from nerve disorders that prevent proper triggering and operation of the bladder, sphincter muscles or nerve disorders that lead to overactive bladder activities or urge incontinence.

In some cases, urinary incontinence can be attributed to improper sphincter function, either in the internal urinary sphincter or external urinary sphincter. For example, aging can result in weakened sphincter muscles, which may cause incontinence. Nerves running though the pelvic floor stimulate contractility in the sphincter. An improper communication between the nervous system and the urethra or urinary sphincter can result in a bladder dysfunction, such as overactive bladder, urgency, urge incontinence, or another type of urinary incontinence.

SUMMARY

In general, the disclosure is directed to techniques and/or systems for identifying and/or treating bladder dysfunction such as urinary incontinence. For example, overactive bladder symptoms may result from the development of coordinated contractions of the detrusor muscle that cause bladder contractions. A clinician may identify one or more focal points of undesirable coordinated contractions at respective locations of bladder tissue (e.g., urothelium, the detrusor muscle, or nerves controlling the detrusor muscle). The focal points correspond to locations that initiate (e.g., cause muscle contractions or originate contractions that are propagated) the undesirable coordinated contractions of the detrusor muscle. Any of a variety of imaging techniques may be used to identify these focal points. A clinician may then target the locations of these identified focal points for ablation therapy, and the clinician may then ablate portions of the bladder tissue corresponding to the locations of the focal points to reduce the coordinated contractions of the detrusor muscle. Targeted ablation of focal points in the bladder tissue may thus alleviate symptoms related to overactive bladder or other disorders related to urinary incontinence.

In one aspect, the disclosure is directed to a method for treating bladder dysfunction in a patient, the method including identifying one or more focal points at respective locations of bladder tissue of a bladder of the patient, the one or more focal points initiating coordinated contractions of a detrusor muscle in the bladder and ablating, for each of the one or more focal points, a respective portion of the bladder tissue at the respective location of the focal point.

In another aspect, the disclosure is directed to a method for treating bladder dysfunction in a patient, the method including selecting first portion of bladder tissue in a bladder of the patient, wherein the first portion corresponds to a first focal point of a plurality of focal points, each focal point of the plurality of focal points being identified as initiating coordinated contractions of a detrusor muscle, ablating the first portion of the bladder tissue, selecting a second portion of the bladder tissue corresponding to a second focal point of the plurality of focal points, and ablating the second portion of the bladder tissue.

In a further aspect, the disclosure is directed to a method for treating bladder dysfunction in a patient, the method including imaging propagation of contractions in a detrusor muscle in a bladder of the patient, mapping, based on the imaged propagation of contractions, one or more focal points at respective locations of bladder tissue, the one or more focal points initiating coordinated contractions of the detrusor muscle, targeting, for each of the one or more mapped focal points of the bladder tissue, respective portions of the bladder tissue, and not targeting portions of the bladder tissue corresponding to non-focal points of the bladder tissue, and ablating, for each of the one or more focal points, the targeted respective portion of the bladder tissue at the respective location of the focal point to reduce the coordinated contractions of the detrusor muscle and overactive bladder symptoms.

In a further aspect, the disclosure is directed to a system for treating bladder dysfunction in a patient, the system including an imaging device configured to identify one or more focal points at respective locations of bladder tissue of a bladder of the patient, the one or more focal points initiating coordinated contractions of a detrusor muscle in the bladder, and an ablation device configured to deliver ablation energy selected to ablate, for each of the one or more focal points, a respective portion of the bladder tissue at the respective location of the focal point.

The details of one or more examples are set forth in the accompanying drawings and the description below. Other features, objects, and advantages will be apparent from the description and drawings, and from the claims.

DETAILED DESCRIPTION

Figure 1:
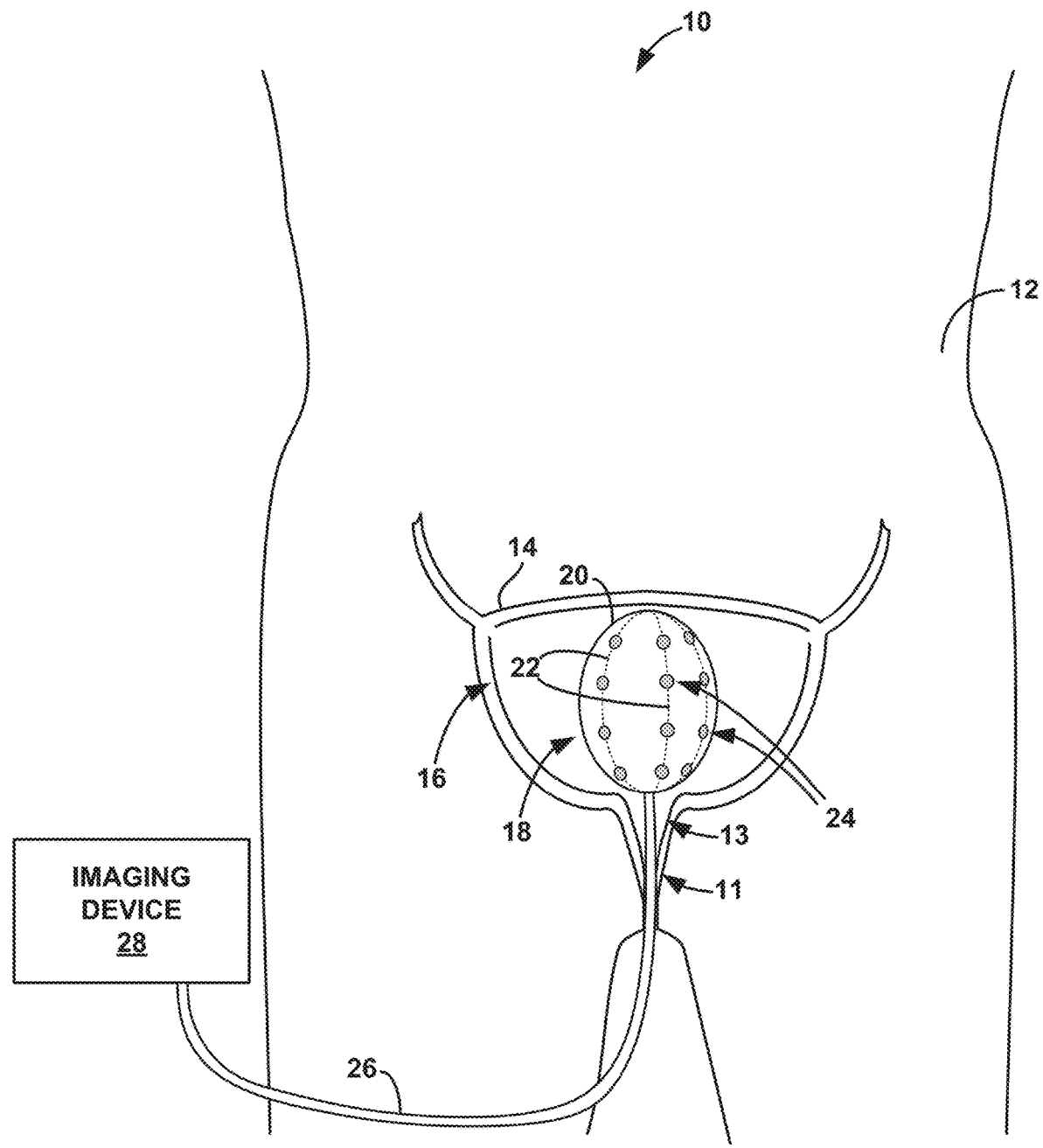
FIG. 1 is a conceptual diagram illustrating an example system that images the bladder to identify focal points in detrusor muscle, according to one or more aspects of this disclosure.

The disclosure is directed to techniques and systems for identifying and/or treating bladder dysfunction. Bladder dysfunction generally refers to a condition of improper functioning of the bladder or urinary tract, and may include, for example, an overactive bladder, urgency, and urinary incontinence. Urgency is a sudden, compelling urge to urinate, and may often, though not always, be associated with urinary incontinence. Overactive bladder may include excessive contractions of the detrusor muscle and may be one of the causes for urgency. Urinary incontinence refers to a condition of involuntary loss of urine, and may include urge incontinence, stress incontinence, or both stress and urge incontinence, which may be referred to as mixed urinary incontinence. As used in this disclosure, the term "urinary incontinence" includes disorders in which urination occurs when not desired, such as stress or urge incontinence (e.g., overactive bladder).

In order to void urine, the nervous system and several muscles of the body typically work in concert to expel urine from the bladder. For example, the internal urinary sphincter muscle and the external urinary sphincter muscle relax to allow urine to pass through the openings in these sphincters. In addition, the detrusor muscle (i.e., smooth muscle residing in the wall of the bladder) contracts to increase the internal bladder pressure and force urine out of the bladder and through the urethra and past the urinary sphincters. Bladder dysfunction can occur when portions of the nervous system that innervate these muscles, or the muscles themselves, prevent the patient from retaining urine until the patient voluntarily decides to urinate.

For example, in healthy patients (e.g., physiologically normal circumstances), the detrusor muscle may produce small muscle contractions that are asynchronous. In other words, these asynchronous (or uncoordinated) muscle contractions are insufficient to generate pressure that forces urine out of the bladder. These uncoordinated muscle contractions may be initiated at various transient (e.g., non-fixed) locations in the detrusor muscle. In contrast, in patients with overactive bladder, the detrusor muscle may produce synchronous (or coordinated) muscle contractions sufficient to generate pressure that forces urine out of the bladder and past the internal and external urinary sphincters without voluntary control from the patient. These muscle contractions sufficient to generate urine voiding pressures may be initiated by one or more focal points that have fixed respective locations in the detrusor muscle. The fixed focal points may develop in bladder tissue (e.g., the detrusor muscle) after spinal cord injury, pelvic floor injury, nerve disorders, aging, or due to other factors.

As described in this disclosure, various techniques and systems may be used to identify fixed focal points within bladder tissue of the bladder and ablate portions of the bladder tissue corresponding to the focal point locations to alleviate overactive bladder symptoms or other causes of urinary incontinence. For example, identifying the focal points may include imaging the propagation of contractions in the detrusor muscle and mapping one or more focal points at respective locations of the bladder tissue according to the imaged propagation of contractions. Imaging techniques may include optical determination of propagation, electrogram generation, optical determination of calcium movement, magnetic resonance imaging, ultrasound imaging, or any other technique configured to detect contractions within the detrusor muscle. In some examples, imaging techniques may include non-invasive imaging techniques such as magnetic resonance imaging or external electrodes to produce electrograms indicative of detrusor muscle activity and/or afferent nerve activity. In some examples, focal point location may be confirmed by temporarily disabling detrusor muscle contractions locally at the one or more identified focal points. If coordinated contractions of the detrusor muscle are reduced, the focal point locations may be confirmed to be accurate.

Once the focal points are mapped to corresponding locations of the bladder tissue, the technique may proceed with targeted ablation of at least one of the corresponding locations of the bladder (e.g., detrusor muscle, urothelium, and/or innervating nerves of the detrusor muscle). In other words, the ablation of the bladder is limited to one or more of only those portions of the bladder that correspond to the identified focal points. This targeted ablation technique may improve efficacy of the ablation therapy and minimize the volume of treated tissue. Although ablation if the detrusor muscle is generally described herein as an example, ablation of focal points may include the ablation of one or more structures of bladder tissue such as urothelium (e.g., the inner lining of the bladder), detrusor muscle, and/or nerves that innervate or control the detrusor muscle. Ablation of the focal points of the urothelium and/or detrusor muscle may be performed by inserting an ablation instrument into the bladder via the urethra and ablating an inner surface of the detrusor muscle. In addition, or alternatively, a portion of one or more nerves residing external to the detrusor muscle (e.g., on the outside of the bladder) and innervating the focal points in the detrusor muscle may be ablated. This targeted ablation may thus ablate portions of the detrusor muscle corresponding to the identified focal points instead of non-focal points of the detrusor muscle. Example ablation techniques may include chemical ablation, radio frequency ablation, ultrasound ablation, mechanical ablation, heat ablation, cyroablation, or other processes for damaging targeted muscle cells. Targeted ablation of focal points in the bladder tissue may thus alleviate symptoms related to overactive bladder or other disorders related to urinary incontinence. In other words, targeted ablation of focal points may desynchronize contractions of the detrusor muscle.

Although the techniques primarily described in this disclosure are for treating bladder dysfunction, the techniques may also be applied to treat other pelvic floor disorders or disorders relating to other organs, tissues or nerves of the patient. For example, the devices, systems, and techniques described in this disclosure alternatively or additionally may be utilized to manage fecal urgency or fecal incontinence.

FIG. 1 is a conceptual diagram illustrating an example system 10 configured to image bladder 14 to identify focal points in detrusor muscle 16. As described herein, system 10 may be configured to image or analyze the detrusor muscle 16 within bladder 14. Uncoordinated contractions in detrusor muscle 16 may be typical for a healthy bladder as they do not lead to unintended voiding events. However, coordinated contractions in detrusor muscle 16 may result in larger contractions of bladder 14 and contribute to symptoms of overactive bladder in patient 12. System 10 may be configured to identify one or more focal points in bladder tissue of bladder 14 via imaging bladder 14 during these contractions of the detrusor muscle. After the locations of each focal point are imaged and mapped, a clinician may then target locations of the identified one or more focal points in the bladder tissue and selectively ablate, or otherwise selectively treat, those target locations of the bladder tissue. This selective ablation of bladder tissue may eliminate the identified focal points while minimizing any effects to other areas of bladder tissue such as urothelium and detrusor muscle 16. The coordinated contractions of bladder 14, and symptoms of overactive bladder, may be reduced or eliminated via the removal of the identified focal points.

The examples herein generally describe the identification of focal points in detrusor muscle 16 and the targeted ablation of portions of detrusor muscle 16. However, focal points may be identified within one or more structures of bladder tissue (e.g., tissue associated with bladder 14) and ablation may be targeted to those focal points of the bladder tissue. For example, locations of urothelium (e.g., the tissue that lines the interior of bladder 14) may be focal points that initiate coordinated contractions of detrusor muscle 16). In other examples, nerves that innervate or control detrusor muscle 16, such as nerve endings disposed on the exterior surface of bladder 14, may be identified as including focal points. In this manner, bladder tissue may include urothelium, detrusor muscle 16, or nerves innervating detrusor muscle 16.

In the example of FIG. 1, therapy system 10 includes imaging device 28, catheter 26, and expandable device 18. Expandable device 18 may include one or more components used to image bladder 14. Expandable device 18 may be attached to catheter 16 and carry one or more sensors, such as an array of electrodes 24 disposed on expandable balloon 20. For example, expandable device 18 may carry a plurality of electrodes 24 (e.g., an array of electrodes 24) along an exterior surface of balloon 20. Expandable device 18 may have two configurations: a collapsed configuration and an expanded configuration.

Expandable device 18 may be configured to be in the collapsed state having a small diameter (e.g., small enough for insertion into a urethra) to allow expandable device 18 to be inserted through the urethra and past urinary sphincter 11 and into bladder 14 via bladder neck 13. Once expandable device 18 is positioned within bladder 14 as shown in FIG. 1, balloon 20 of expandable device 18 may be expanded from the collapsed state and into the expanded state. In the expanded state, the exterior surface of balloon 20 and electrodes 24 may contact the inner surface of bladder 14. However, not all of electrodes 24 or the entire exterior surface of balloon 20 may need to be in contact with the wall of bladder 14. In one example, and as shown in FIG. 1, balloon 20 may be constructed of an elastic material such as a polymer to form the balloon-like structure to which electrodes 24 are attached. A gas (e.g., nitrogen or room air) or a liquid (e.g., saline or water) may be pumped from imaging device 28 (or another device), through catheter 26, and into balloon 20. Increased pressure from the pumping of air or liquid into balloon 20 may cause balloon 20 to increase in size and expand until the appropriate expanded state has been reached.

Once expandable device 18 is configured in the expanded state, imaging device 28 may sense electrical signals from electrodes 24 that are in contact with the inner surface of bladder 14 and detrusor muscle 16. Each of electrodes 24 may be coupled to imaging device 28 via respective electrical conductive wires 22. In this manner, imaging device 28 may generate an electrogram for the changes in electric potential between the different pairs of electrodes 24. In the example of FIG. 1, electrodes 24 may sense intrinsic signals via a bipolar or multipolar configuration (e.g., between electrodes 24). In other examples, electrodes 24 may function in a unipolar or monopolar configuration with a ground pad placed on the exterior skin surface of patient 12 or other ground electrode placed within an opening of patient 12 (e.g., within the rectum).

As muscle fibers in detrusor muscle 16 depolarize, imaging device 28 may thus detect locations of lesser and greater depolarizations and how the depolarizations change over time. In other words, each electrode, or pairs of electrodes, could be used by imaging device 28 to generate individual electrogram channels for the respective locations within bladder 14. Using this depolarization information, imaging device 28 may generate a map of one or more focal points for the contractions of detrusor muscle 16 resulting from the depolarizations in detrusor muscle 16. The map may thus identify locations of the focal points within detrusor muscle 16. For example, imaging device 28 may generate the map by identifying the largest depolarization magnitudes as focal points. Alternatively, imaging device 28 may track depolarizations over time to identify the synchronization of muscle fibers and indicate the time-wise starting locations of the depolarizations as respective focal points. Imaging device 28 may orient, or register, the locations of the focal points to one or more identifiable structures within bladder 14, such as the ureteral openings or identifiable signals from adjacent organs (e.g., the bowel or abdominal muscles) or even an artificial marking electrical signal provided to the exterior of patient 12 during the mapping process. In some examples, imaging device 28 may even implant a radiopaque marker or other identifier to which the map of focal points can be registered and used to identify the focal points for ablation therapy. In other examples, a clinician may manually map the focal points from the electrogram information based on electrograms from the electrodes 24 or another imaging modality.

Although balloon 20 of expandable device 18 may be generally spherical or elliptical, balloon 20 may form any symmetrical or irregular volumetric shape in the expanded state. Balloon 20 may be configured to assume the approximate shape of the inside volume of bladder 14 in some examples. In an alternative example, expandable device 18 may be constructed of a wire structure, instead of balloon 20, that is expanded from the collapsed state via a change in strut configuration (e.g., sliding filaments that force the structure to increase in volume or pre-sprung structures that expand when pushed out of a constrictive sleeve or catheter 26) or changes in temperature that cause the wire structure (e.g., a memory metal such as a nickel-titanium alloy or Nitinol) to alter its configuration and expand in volume such that electrodes 24 can contact the inner surface of bladder 14. In other examples, system 10 may utilize non-expanding devices to position sensors at desired locations within bladder 14. For example, a plurality of different leads may be extended out from the end of catheter 26 such that each of the different leads carries a subset of the electrodes 24 to a different location along the inner wall of bladder 14. These alternative examples may carry sensors (e.g., electrodes 24) similar to balloon 20.

Once imaging device 28 has mapped and identified the focal points of detrusor muscle 16 contractions (an imaging modality has identified initiation locations for depolarizations in detrusor muscle 16), expandable device 18 may be deflated or otherwise contracted back into the collapsed state for removal from bladder 14. A clinician may use the mapped focal points to selectively target and ablate the locations of detrusor muscle 16 that correspond to the focal points, as further described herein. In some examples, the imaging process described herein for identifying and mapping focal points may be performed after a selective ablation process to ensure that the focal points have been removed and/or identify any remaining focal points that still require treatment. In this manner, the imaging and ablation process may require multiple iterations to complete the selective ablation of focal points in detrusor muscle 16 for some patients.

Electrodes 24 attached to, or otherwise carried on, expandable device 18 may be constructed with a cylindrical shape and may be spaced equidistant around expandable device 18. However, electrodes 24 may be constructed with other non-circular shapes in other examples. Electrodes 24 may also be positioned in such a manner than they are not equidistant around expandable device 18. For example, electrodes 24 may be positioned on arcs or in staggered locations to achieve appropriate coverage of detrusor muscle 16 activity in the expanded state. Expanding device 18 may include any number of electrodes 24 appropriate to image the entire detrusor muscle 16. A greater number of electrodes 24 may allow imaging device 28 to generate electrograms of greater resolution and achieve more precise locations of any focal points in detrusor muscle 16. For example, expandable device 18 may carry between 2 electrodes and 100 electrodes 24. In some examples, expandable device 18 may between 8 electrodes and 20 electrodes 24. However, expanding device 18 may be configured to carry any number of electrodes as needed to image bladder 14.

Although electrodes are described as being used to generate an electrogram and image detrusor muscle 16, expandable device 18 or another insertable device may carry one or more different sensors. Different sensors may include ultrasound transducers, optical sensors, chemical sensors, pressure sensors, or any other sensors configured to detect muscle activity. For example, imaging detrusor muscle 18 may include at least one of optically determining the propagation of contractions, obtaining electrogram information for the propagation of contractions, optically determining calcium movement for the propagation of contractions, or ultrasound imaging of the propagation of contractions. In alternative examples, exterior imaging techniques may be used such as magnetic resonance imaging the propagation of contractions. In another example, an array of pressure sensors (e.g., force transducers, strain gauges, etc.) on balloon 20 (instead of or in addition to other sensors such as electrodes 24) may be configured to contact the bladder wall and detect pressure waves due to the contractions and track the propagation of contractions. Imaging device 28 may be configured to interpret the output from each pressure sensor such that focal points may be identified.

System 10 may also include imaging device 28. Imaging device 28 may be coupled to electrodes 24 (or other sensors) via a wired connection through catheter 26. In other examples, imaging device 28 may be in wireless communication with electrodes 24 of expandable device 18. Imaging device 28 may include a processor that controls a sensing module to obtain the electrogram from detrusor muscle 16. Imaging device 28 may also include a user interface that receives input from a user (e.g., a clinician or technician) and/or outputs data related to the obtained information and identified focal points in detrusor muscle 16. In some examples, the user interface includes, for example, a keypad and a display, which may for example, be a cathode ray tube (CRT) display, a liquid crystal display (LCD) or light emitting diode (LED) display. The keypad may take the form of an alphanumeric keypad or a reduced set of keys associated with particular functions. Imaging device 28 can additionally or alternatively include a peripheral pointing device, such as a mouse, via which a user may interact with the user interface. In some examples, a display of imaging device 28 may include a touch screen display, and a user may interact with imaging device 28 via the display. It should be noted that the user may also interact with imaging device 28 remotely via a networked computing device. In other examples, imaging device 28 may interface with a separate computing device (e.g., a mobile computing device or workstation) that interfaces with the clinician.

For example, the user may use imaging device 28 to obtain the sensed contraction information from detrusor muscle 16. In some examples, imaging device 28 may output the raw imaging information (e.g., electrograms), locations of identified focal points, and/or a map of the identified focal points. In this manner, imaging device 28 may generate a graphical map of the electrogram information that illustrates which locations of detrusor muscle 16 are likely the locations of focal points causing the coordinated contractions of the detrusor muscle. In other words, hot spots of muscle activity (e.g., locations having larger depolarizations and/or depolarizations earlier in time than surrounding locations) may be identified as focal points that initiate each coordinated contraction.

In this manner, system 10 may be used in a method for treating bladder dysfunction in patient 12. System 10 may identify, or assist a clinician in identifying, one or more focal points at respective locations of detrusor muscle 16 in bladder 14 of patient 12. The one or more focal points may initiate coordinated contractions of detrusor muscle 16. A clinician may then ablate, for each of the one or more focal points, a respective portion of detrusor muscle 16 at the respective location of the focal point to treat patient 12. In some examples, a set of focal points may initiate the coordinated contractions of detrusor muscle 16, where the coordinated contractions of the detrusor muscle promote an overactive bladder condition of patient 12. The one or more identified focal points at which tissue is to be ablated may include all of the focal points in the set of focal points or only include a subset of the set of focal points. In this manner, selective ablation of portions of detrusor muscle 16 corresponding to focal points may not be completed for every focal point from which coordinated contractions are initiated in the detrusor muscle.

As discussed above, identifying the one or more focal points in detrusor muscle 16 may include imaging the propagation of contractions in the detrusor muscle and mapping, based on the imaged propagation of contractions, the one or more focal points at the respective locations of detrusor muscle 16. The mapping process may include creating an indication of where each of the focal points is located with respect to each other and/or with respect to one or more landmarks within bladder 14. The resulting map may be numerical, graphical, or otherwise descriptive of the focal point locations. In some examples, the map may include coordinate locations that can be input to a surgical assist machine that assists the clinician in the ablation of the portions of detrusor muscle 16 corresponding to the identified focal points.

In some examples, a clinician may test the identified focal points to confirm that each of the focal points is initiating coordinated contractions. For example, prior to ablating portions of detrusor muscle 16 corresponding to respective focal points, the clinician may inject a substance into at least one of the respective portions of detrusor muscle 16. The substance may be configured to temporarily disable initiation of contractions. Example substances may include a drug prepared from the bacterial toxin botulin (e.g., Botox®), an injectable local anesthetic such as lidocaine, or a topical anesthetic appropriate for use in bladder 14. The clinician may then confirm that the substance reduces coordinated contractions of detrusor muscle 16 from the treated focal points. The clinician may monitor patient symptoms related to urinary function or even re-image detrusor muscle 16 with system 10 for evidence of uncoordinated or coordinated contractions. Responsive to the confirmation that the substance temporarily disables initiation of detrusor muscle contractions, the clinician may ablate the respective portions of the detrusor muscle corresponding to the identified focal points.

As discussed herein, a clinician or technician may insert an ablation instrument into bladder 14 via the urethra and direct the selective ablation to the inner surface of detrusor muscle 16 via the ablation instrument located in bladder 14 when ablating the respective portions of the detrusor muscle. In this manner, the ablation therapy may be completed via a minimally invasive procedure via the urethra. The ablation instrument may include a catheter that is guided through the urethra and into bladder 14. This ablation will be referred to as targeted ablation or selective ablation. In other words, ablation of detrusor muscle 16 includes targeting ablation for only the respective portions of the detrusor muscle corresponding to the identified focal points instead of non-focal points within the detrusor muscle 16. Therefore, the targeted ablation may reduce coordinated contractions of detrusor muscle 16 while maintaining the integrity of the remaining detrusor muscle.

In some examples, the ablation process may be iterative for multiple focal points. For example, the method for treating bladder dysfunction may include targeting a first portion of detrusor muscle 16 in bladder 14 of patient 12, wherein the first portion of detrusor muscle 16 corresponds to a first focal point of a plurality of focal points. Each focal point of the plurality of focal points has been identified, e.g., by imaging, as initiating coordinated contractions of detrusor muscle 16. A clinician may then ablate the first portion of detrusor muscle 16. If there are more focal points to address, the clinician may continue by targeting a second portion of detrusor muscle 16 that corresponds to a second focal point of the plurality of focal points and ablate the second portion of detrusor muscle 16. As discussed above, one or more anatomical or artificial markers can be used to register the map of focal points and allow the clinician to orient an ablation device to bladder 14 and identified focal points of the map.

The targeted approach to ablation described herein may be contrasted with an indiscriminate "carpet-bombing" approach in which many areas of detrusor muscle 16 are ablated or treated without regard as to the location of focal points. The targeted ablation approach described herein may thus effectively terminate focal points and coordinated contractions while minimizing damage to other areas of detrusor muscle 16 and bladder 14.

Although ablation of focal points may be completed via ablation applied to the inner surface of bladder 14, other ablation techniques may be used in other examples. For example, a clinician may target the identified focal points via treatment exterior to bladder 14. The clinician may use an ablation system to ablate a portion of one or more nerves that reside external to detrusor muscle 16 and control at least a portion of detrusor muscle 16 associated with at least one of the one or more focal points. The ablation of the portion of the one or more nerves may disrupt the communication with a portion of detrusor muscle 16 and eliminate or reduce to coordinated contractions initiated by a focal point at that location of detrusor muscle 16. Ablation of a portion of a nerve external to bladder 14 may require a minor incision or laparoscopic procedure to reach the desired portion of the nerve. Other ablation techniques may also be used to treat an identified focal point in detrusor muscle 16.

Ablation, as described here, may include any technique that destroys and/or removes targeted tissue. For example, ablation may include radio frequency ablation, chemical ablation, ultrasound ablation, mechanical ablation, heat ablation, or cyroablation. In any of these techniques, the portion of detrusor muscle 16 or a nerve that corresponds to an identified focal point that initiates coordinated contractions may be damages and/or removed to eliminate or reduce the coordinated contractions.

Figure 2A:
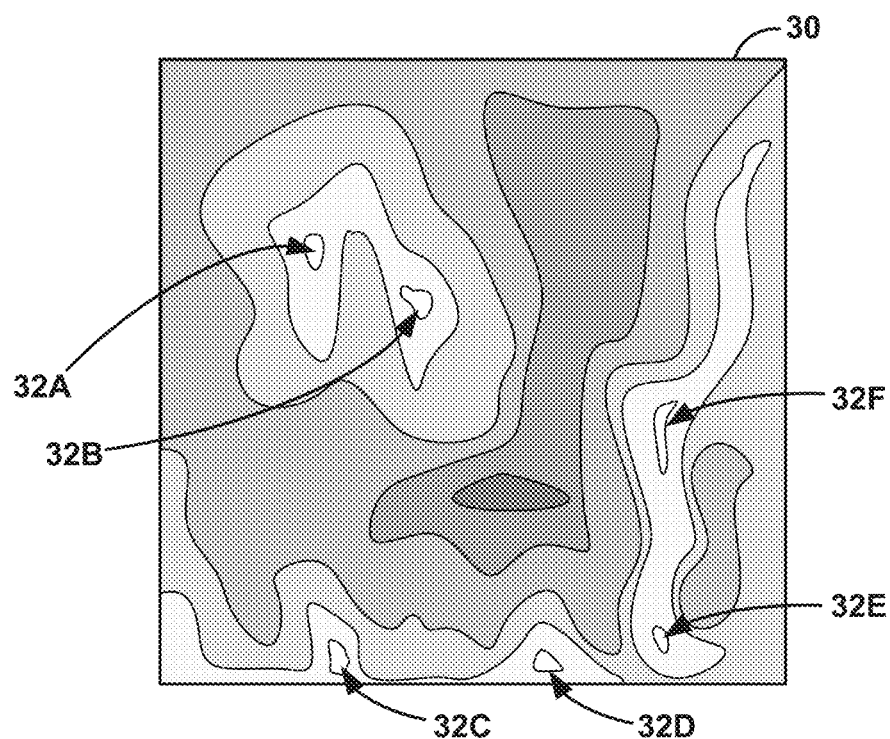
FIGS. 2A and 2B are illustrations of example maps showing initiation locations for contractions in detrusor muscle.
Figure 2B:
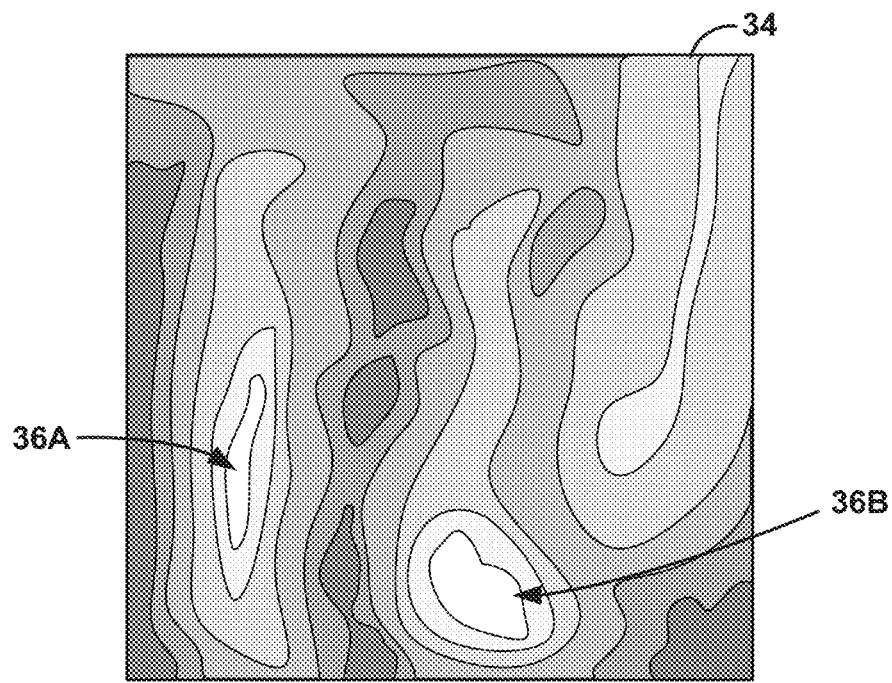

FIGS. 2A and 2B are illustrations of example maps 30 and 34 showing initiation locations for contractions in detrusor muscle. Maps 30 and 34 may be generated by imaging device 28 of FIG. 1, for example, using one or more imaging techniques. However, in contrast to the example of FIG. 1, imaging device 28 may be configured to image changes in calcium ions for calcium imaging in the example of FIGS. 2A and 2B. Imaging device 28 may generate maps 30 and 34 by imaging propagation of contractions in detrusor muscle 16 and then mapping, based on the imaged propagation of contractions, the one or more points at the respective locations of detrusor muscle 16. The different shaded areas in each of maps 30 and 34 illustrate different levels of contraction, such as the number of transient calcium ions in calcium imaging. In this manner, maps 30 and 34 may be referred to as isochronal maps with isolines indicating changes to the value of a detected parameter. The closer that different shaded areas are together (e.g., closer isolines) indicate greater contraction in detrusor muscle 16.

As shown in FIG. 2A, map 30 indicates multiple variable initiation locations in detrusor muscle 16 resulting in uncoordinated contractions. Map 30 may be indicative of a patient with normal bladder activity or no overactive bladder symptoms. Initiation locations 32A, 32B, 32C, 32D, 32E, and 32F (collectively "initiation points 32") show that detrusor muscle 16 contractions have been initiated at multiple different locations (six locations in the example of FIG. 2A). Initiation locations 32 are also relatively small and the gradient between initiation locations 32 is relatively small. From this information, map 30 indicates that none of initiation locations 32 are focal points for coordinated contractions. Instead, map 30 indicates that detrusor muscle 16 is showing uncoordinated contractions.

In contrast to FIG. 2A, FIG. 2B shows map 34 that indicates a few initiation locations in detrusor muscle 16 resulting in coordinated contractions. Map 34 may be indicative of a patient with overactive bladder caused by, at least in part, coordinated contractions of detrusor muscle 16.

Initiation locations 36A and 36B (collectively "initiation locations 36") show that detrusor muscle 16 contractions have been initiated at only two different locations in the example of FIG. 2B. Initiation locations 36 can thus be referred to as focal points because they are relatively large and the gradient between initiation points 36 is also relatively large. In other words, the isolines between initiation locations 36 are close together to indicate contractions in detrusor muscle 16. Therefore, from this information, map 34 indicates that both of initiation locations 36 are focal points that initiate the coordinated contractions of detrusor muscle 16.

In comparing map 30 of FIG. 2A to map 34 of FIG. 2B, it is clear that the fewer initiation locations 36 of map 34 and the closer isolines of map 34 indicate that map 34 is showing coordinated contractions of detrusor muscle 16. These contractions are thus initiated by initiation locations 36 that are focal points in detrusor muscle 16. Imaging device 28 or a clinician may determine that an initiation point is a focal point in response to determining that an area within the isolines of initiation points exceeds a threshold and/or when the identified number of initiation points are below a threshold number of initiation points for a given area of detrusor muscle 16.

From the information provided in map 34 of FIG. 2B, a clinician may target ablation to the portions of detrusor muscle 16 that correspond to the locations of initiation locations 36A and 36B. Ablation of the detrusor muscle at these locations, and only these locations, may prevent or reduce the number of coordinated contractions of detrusor muscle 16 without damaging additional muscle or tissue of bladder 14. Although maps 30 and 34 show isochonal maps, initiation locations, including focal points, may be mapped in any number of methods. Imaging device 28 may generate graphical indications of only suspected focal points, indications of the direction in which contractions emanate from initiation locations, color maps of muscle contraction intensity, or even numerical values for various coordinates within space representing detrusor muscle 16.

Figure 3:
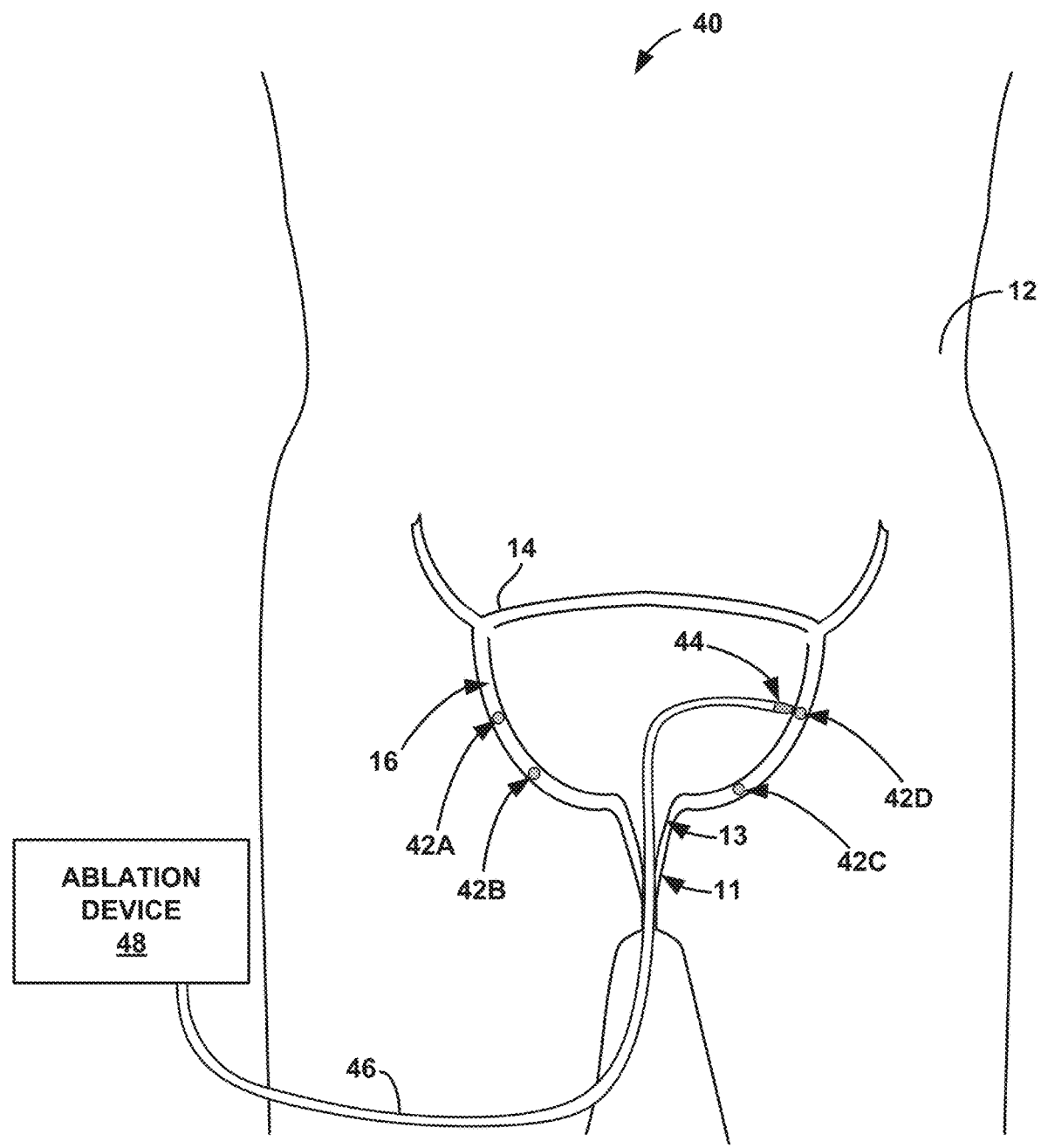
FIG. 3 is a conceptual diagram illustrating an example system that ablates targeted portions of detrusor muscle in the bladder, according to one or more aspects of this disclosure.

FIG. 3 is a conceptual diagram illustrating an example system 40 that is configured to ablate targeted portions of detrusor muscle 16 in bladder 14. As shown in FIG. 3, ablation system 40 includes ablation electrodes 44, catheter 46, and ablation device 48. Ablation device 48 may include a radio frequency (RF) generator that generates the electrical energy delivered to ablation electrodes 44 (e.g., a bipolar pair of electrodes) via conductors housed within catheter 46. In other examples, one or more unipolar electrodes 44 may be used in conjunction with a ground pad or other return electrode. Ablation device 28 may also include a user interface that is configured to receive user inputs controlling ablation device 48 and output an indication of the ablation process, such as the time of ablation, the temperature adjacent ablated tissue, and other related information from one or more sensors carried by catheter 46.

Catheter 46 may be flexible and constructed of a biocompatible material. The one or more conductors within catheter 46 may couple the RF generator within a housing of ablation device 48 with the electrodes 44. In some examples, catheter 46 may carry additional sensors such as temperature sensors or impedance sensors configured to monitor tissue during ablation. Catheter 46 may also include an optical sensor configured to obtain visual information from the distal end of catheter 46. For example, the optical sensor may provide video information that is displayed to the clinician such that the clinician can navigate electrodes 44 to the appropriate locations of bladder 14 that correspond to respective focal points in detrusor muscle 16. Alternatively, catheter 46 may include a channel in which a cystoscope can be inserted to allow the clinician to view tissue at the end of catheter 46.

Electrodes 44 may be constructed of any shape appropriate for delivering RF energy to detrusor muscle 16 and ablate tissue of the focal points. In one example, electrodes 44 may be disks or rounded ends disposed at the tip of catheter 46 configured to contact the inner surface of bladder 14. In another example, electrodes 44 may be configured as needles that are extendable from catheter 46. Needle electrodes may be configured to penetrate into detrusor muscle 16 such that RF energy is delivered directly to muscle tissue instead of through the interior of bladder 14. Other shapes of electrodes 44 may be used in other examples. Multiple electrodes 44 may provide bipolar ablation. In some examples, a ground pad maybe applied to the exterior of patient 12 (e.g., on an abdominal skin surface or lower back skin surface) such that one or more electrodes 44 within bladder 14 may provide unipolar (or monopolar) RF ablation. System 40 may be configured to provide both bipolar and unipolar ablation, selected based on the size and/or shape of desired lesion.

As discussed herein, focal points in detrusor muscle 16 may be previously identified via an imaging device. Identified focal points 42A, 42B, 42C, and 42D (collectively "focal points 42") are shown in FIG. 3 as portions of detrusor muscle 16 targeted for ablation. Although four focal points 42 are shown in the cross-section of bladder 14 in FIG. 3, additional focal points may be located at other locations not shown in the example of FIG. 3. Treatment of the overactive bladder symptoms of patient 12 may include ablation of the portions of detrusor muscle 16 that correspond to focal points 42.

A clinician may insert electrodes 44 and catheter 46 (e.g., an ablation instrument) into bladder 14 via the urethra and direct electrodes 44 to an inner surface of detrusor muscle 16 via catheter 46. In some examples, catheter 46 may include a guide wire or other mechanism for bending or otherwise moving catheter 46 to a desired location within bladder 14. For example, as shown in FIG. 3, the clinician may direct electrodes 44 to focal point 42D. The clinician may then interact with a user interface of ablation device 48 to start the ablation process. Ablation therapy may begin when an RF signal (e.g., RF energy) is transmitted between the two electrodes 44 located at the distal end of catheter 46, e.g., in a bipolar arrangement. Since both of electrodes 44 are in contact with bladder 14, this RF signal may increase the heat of tissue adjacent to electrodes 44 until tissue necrosis occurs and ablation of the targeted area is complete.

In addition, each location for ablation (e.g., the respective focal points 42) may receive a series of ablation events delivered in order to treat that identified focal point. In some examples, imaging may be performed between each ablation event of the series of events as feedback to ensure that the identified focal point has been treated to reduce or eliminate the coordinated contractions of the detrusor muscle.

Catheter 46 may be sized for insertion via the urethra. In some examples, catheter 46 may have a diameter of approximately 7 French (2.33 mm), 8 French (2.67 mm), or 9 French (3.00 mm). One or more electrodes 44 may cover an area at or near the tip of catheter 46 that is approximately the size of the cross-section of catheter 46. However, the one or more electrodes 44 may be smaller or larger than the cross-section of catheter 46 in other examples. Using the one or more electrodes 44, the clinician may create lesions (i.e., ablated tissue areas) between approximately 1 mm and 10 mm in diameter. However, smaller or larger lesions may be used in other examples. In some examples, the lesion may be approximately the area of the area of the one or more electrodes 44. The size of catheter 46 and electrodes 44 may be similar for other ablation devices and techniques described herein. Alternatively, the distal end or tip of catheter 46 may include an expandable element (e.g., one or more balloons, stent-like structures, scaffolding, etc.) that includes one or more electrodes having an ablative area greater than the cross-section of catheter 46. In any event, the size of the lesion created may correspond to the size needed to ablate each of the respective focal points 42.

Completion of the targeted ablation of the portion of detrusor muscle 16 corresponding to focal point 42D may be determined in response to exceeding a threshold temperature of the tissue, exceeding a threshold impedance, or visual confirmation that the tissue has been ablated. Once ablation of focal point 42D is complete, the clinician may sequentially move electrodes 44 to other focal points 42 and ablate those portions of detrusor muscle 16 until all focal points are eliminated. In this manner, ablation of portions of detrusor muscle 16 that correspond to focal points 42 is referred to as targeted or selective ablation because tissue corresponding to focal points 42 is ablated instead of non-focal points of detrusor muscle 16. In other words, portions of detrusor muscle 16 that do not include the identified focal points 42 remain unablated.

System 40 is described as providing ablation therapy via the delivery of RF energy to target tissue. However, system 40 may be configured to ablate target tissue using other techniques. For example, catheter 46 may be configured to deliver a chemical to target tissue locations that achieves tissue necrosis. In another example, ablation device 48 may energize one or more ultrasound transducers disposed on catheter 46 that provide ultrasound ablation of the target tissue. In other examples, catheter 46 may carry a heating element that provides heat ablation, carry a tissue removal tool configured to mechanically remove the target portion of detrusor muscle 16, or deliver low temperature fluid configured to provide cryoablation of the target tissue. In this manner, system 40 may be configured to provide different types of ablation therapy.

Ablation system 40 and imaging system 10 of FIG. 3 are described as different systems. In other words, the clinician may need to insert expandable device 18 to image detrusor muscle 16, remove expandable device 18, and then insert catheter 46 of system 40 to perform the ablation of identified focal points. However, in other examples, the functionality of imaging system 10 and ablation system 40 may be combined such that only one multifunctional device must be inserted into bladder 14. For example, expandable device 18 may include electrodes that sense contractions of detrusor muscle 16 and electrodes configured to deliver RF ablation energy. In other examples, the catheter that is inserted into bladder 14 may include both expandable device 18 of system 10 and a catheter that carries electrodes 44 of system 40.

In some examples, the clinician may confirm the accuracy of the identified focal points 42 prior to ablating the corresponding portions of detrusor muscle 16. The clinician may, prior to ablating the respective portions of detrusor muscle 16, apply a substance into at least one of the respective portions of detrusor muscle 16 corresponding to the identified focal points 42. The substance may be configured to temporarily disable initiation of contractions. In response to obverting a reduction or elimination of coordinated contractions from the applied substance, the clinician may confirm that the substance reduces coordinated contractions of detrusor muscle 16. Responsive to the confirmation, the clinician may proceed to ablate the respective portions of detrusor muscle 16. The substance may be applied topically to the inner surface of bladder 14 or injected to the target location of detrusor muscle 16.

Figure 4:
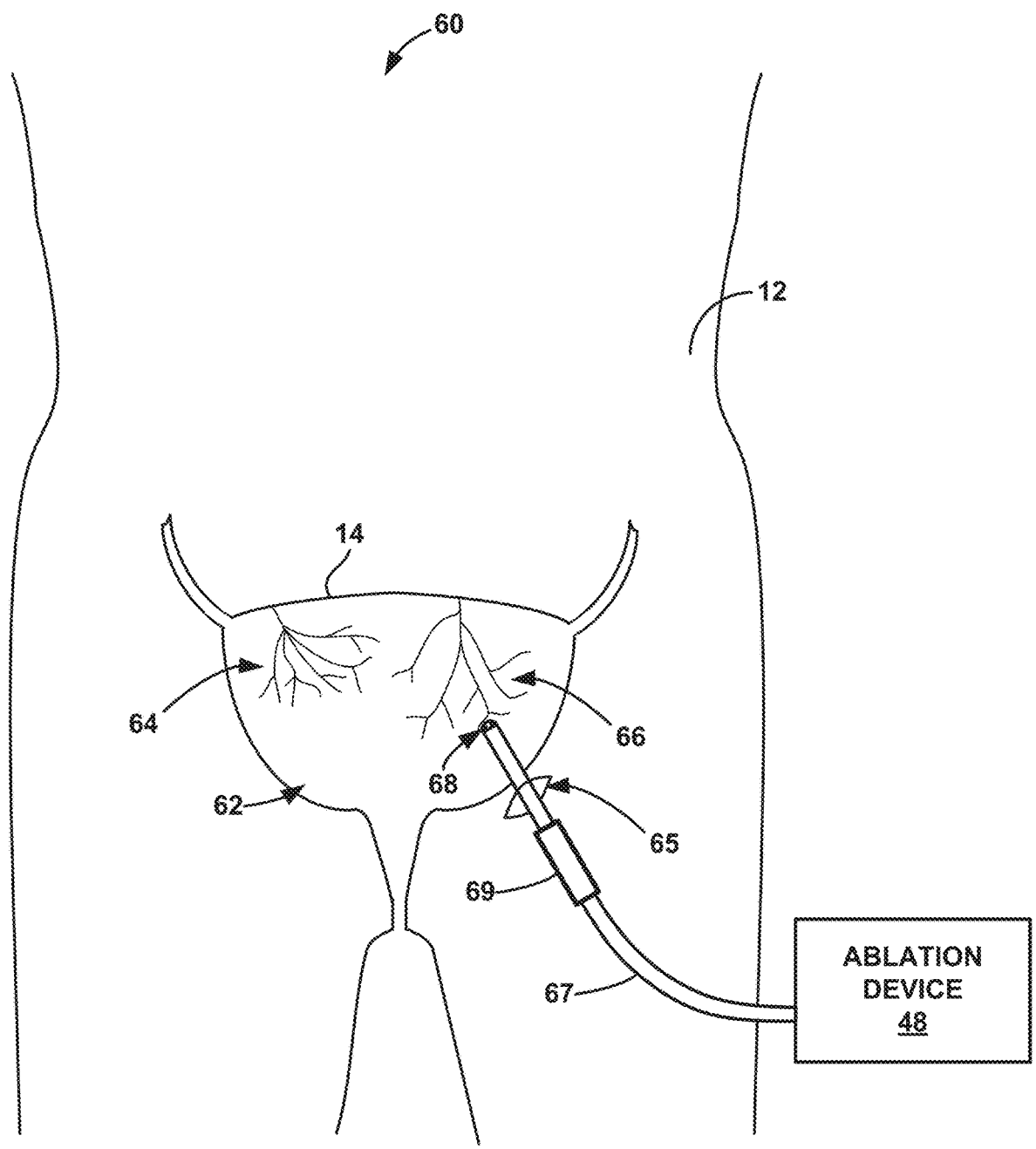
FIG. 4 is a conceptual diagram illustrating an example system that ablates targeted portions of nerve or muscle tissue external of the bladder, according to one or more aspects disclosed herein.

FIG. 4 is a conceptual diagram illustrating an example system 60 configured to ablate targeted portions of nerve or muscle tissue external of bladder 14. System 60 may be similar to system 40 described in FIG. 3. However, system 60 may be configured to ablate portions of nerves external to bladder 14. Ablation device 48 may be the same device described in FIG. 3, but catheter 67 and electrodes 65 may be configured for ablating portions of nerves that innervate fibers of the detrusor muscle corresponding to the identified focal points.

Catheter 67 may be configured to be inserted through an opening 65 in the skin of patient 12 (e.g., via a laparoscopic procedure) and deliver electrodes 68 to the desired tissue location. The distal end of catheter 67 may carry one or more electrodes 68 configured to delivery RF energy to tissue. Electrodes 68 may be surface electrodes that contact a desired tissue or shaped as needles that penetrate into tissue. Electrodes 68 may be configured to provide bipolar ablation or unipolar ablation. A ground pad may also be electrically coupled to ablation device 48 for the one or more unipolar electrodes 68, and the ground pad may be placed at an external location of the skin of patient 12. Catheter 67 may also include one or more conductors (e.g., wires) that electrically couple each electrode 68 to ablation device 48. Handle 69 may provide a surface to which the clinician can grab and manipulate catheter 67 during ablation.

Bladder 14 includes a detrusor muscle (not shown in FIG. 4) that generates contractions to cause bladder 14 to pressurize urine within bladder 14. Nerve fibers innervating the detrusor muscle may include sympathetic and parasympathetic fibers and branch from the hypogastric plexuses and nerves, the pelvic splanchnic nerves, and the inferior hypogastric plexus. Example nerve branches 64 and 66 shown on the exterior surface 62 of bladder 14 are shown in FIG. 4. One or more portions of nerve branches 64 and/or nerve branches 66 may be ablated to prevent the occurrence of identified focal points.

A clinician may ablate a portion of a nerve by first inserting the distal end of catheter 67 into patient 12. The clinician may insert catheter 67 through a surgically opened area of skin or various laparoscopic techniques. The clinician may then navigate the distal end of catheter 67 to a nerve that innervates one of the identified focal points in the detrusor muscle, such as a portion of nerve branches 66. The clinician may identify the appropriate nerve via visual identification and/or identification via electrogram, for example. Other identification methods are also possible. Once the clinician has positioned electrodes 68 in contact with the targeted portion of nerves 66, the clinician may start delivery of RF energy from ablation device 48 and ablate the portion of the nerve residing external to the detrusor muscle. Since this portion of the nerve controls at least a portion of the detrusor muscle associated with at least one of the one or more identified focal points, the associated focal point may be eliminated and reduce coordinated contractions of the detrusor muscle. This process may be iteratively performed until nerves are ablated that affect some or all of the identified focal points. In addition, each location for ablation may receive a series of ablation events delivered in order to treat that targeted portion of the nerves and/or the identified focal point. In some examples, imaging may be performed between each ablation event of the series of events as feedback to ensure that the identified focal point has been treated to reduce or eliminate the coordinated contractions of the detrusor muscle.

Catheter 67 may be sized for insertion through the skin and to the target area to be ablated, such as the targeted portion of nerves 66. In some examples, catheter 67 may have a diameter of approximately 7 French (2.33 mm), 8 French (2.67 mm), or 9 French (3.00 mm). Catheter 67 may be smaller or larger than these example sizes. One or more electrodes 68 may cover an area at or near the tip of catheter 67 that is approximately the size of the cross-section of catheter 67. However, the one or more electrodes 68 may be smaller or larger than the cross-section of catheter 67 in other examples.

Using the one or more electrodes 68, the clinician may create lesions (i.e., ablated tissue areas) between approximately 1 mm and 10 mm in diameter. However, smaller or larger lesions may be used in other examples. In some examples, the lesion may be approximately the area of the one or more electrodes 68. The size of catheter 67 and electrodes 68 may be similar for other ablation devices and techniques described herein. Alternatively, the distal end or tip of catheter 67 may include an expandable element (e.g., one or more balloons, stent-like structures, scaffolding, etc.) that includes one or more electrodes having an ablative area greater than the cross-section of catheter 67. In any event, the size of the lesion created may correspond to the size needed to ablate the portions of nerves that innervate respective focal points.

Although system 60 is described as delivering RF ablation energy, ablation system 60 may be configured to deliver any of the other types of ablation described in this disclosure. In some examples, ablation of a portion of nerves external to bladder 14 may be the only method of reducing or eliminating focal point activity within the detrusor muscle. In other examples, ablation of a portion of the nerves may be performed in addition to the ablation delivered via the interior of bladder 14. In this manner, treatment of overactive bladder described herein may include ablation of portions of the detrusor muscle and/or ablation of one or more nerves that innervate the detrusor muscle.

Figure 5:
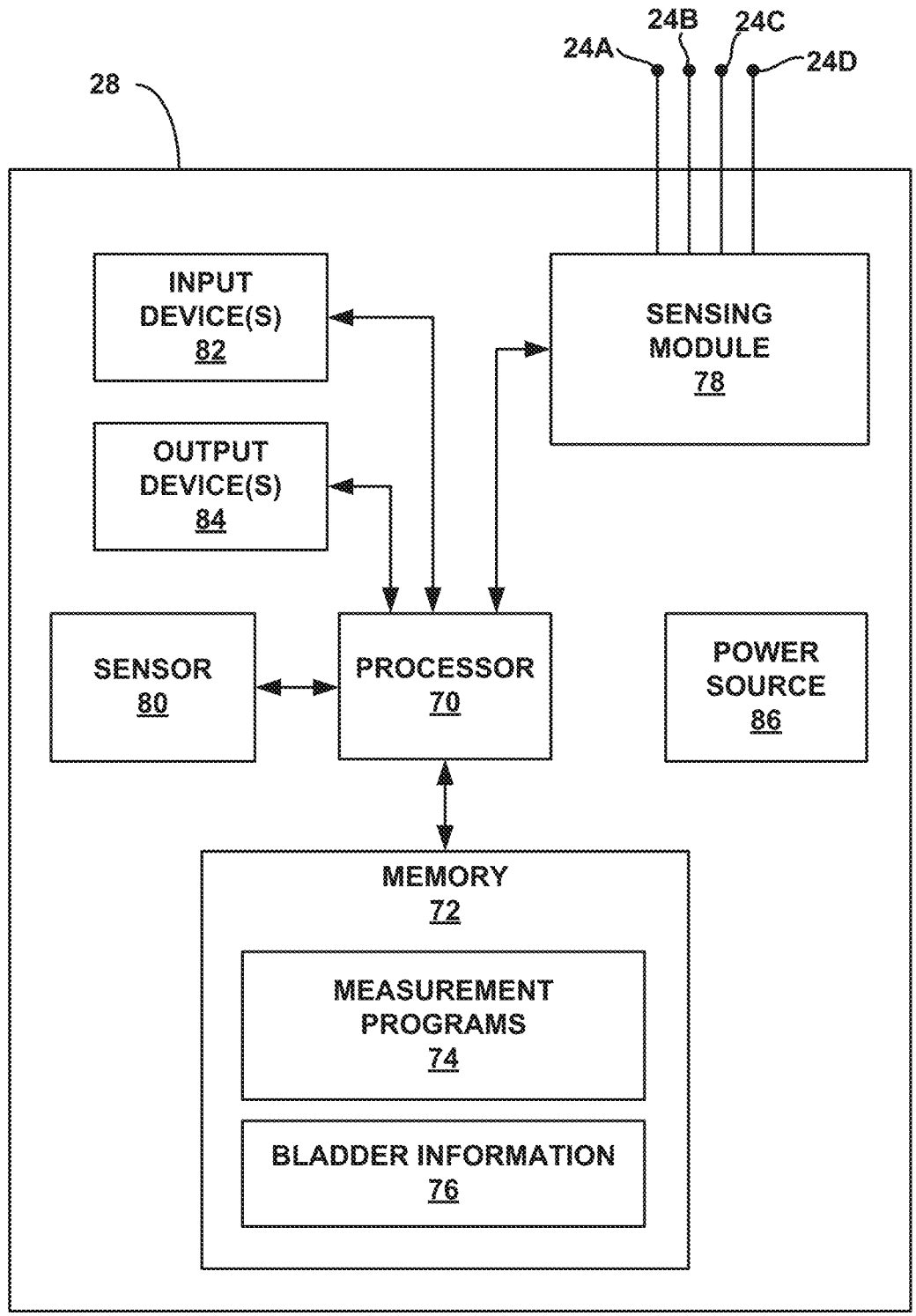
FIG. 5 is a block diagram illustrating an example configuration of an imaging device which may be utilized in the system of FIG. 1.

FIG. 5 is a block diagram illustrating an example configuration of imaging device 28 utilized in system 10 of FIG. 1. In the example of FIG. 5, imaging device 28 includes sensor 80, processor 70, sensing module 78, memory 72, input devices 82, output devices 84, and power source 86. In other examples, imaging device 28 may include more or fewer components. For example, imaging device 28 may include a telemetry module for wirelessly transmitting data or imaging device 28 may not include sensor 80.

In general, imaging device 28 may comprise any suitable arrangement of hardware, alone or in combination with software and/or firmware, to perform the techniques attributed to imaging device 28 and processor 70 and sensing module 78 of imaging device 28. In various examples, processor 70 of imaging device 28 may include one or more processors, such as one or more microprocessors, digital signal processors (DSPs), application specific integrated circuits (ASICs), field programmable gate arrays (FPGAs), or any other equivalent integrated or discrete logic circuitry, as well as any combinations of such components. Imaging device 28 also, in various examples, may include a memory 72, such as random access memory (RAM), read only memory (ROM), programmable read only memory (PROM), erasable programmable read only memory (EPROM), electronically erasable programmable read only memory (EEPROM), flash memory, comprising executable instructions for causing the one or more processors to perform the actions attributed to them. Moreover, although processor 70 and sensing module 78 are described as separate modules, in some examples, processor 70 and sensing module 78 (or more devices of imaging device 28) are functionally integrated. In some examples, processor 70 and sensing module 78 correspond to individual hardware units, such as ASICs, DSPs, FPGAs, or other hardware units.

Memory 72 stores information such as data for the operation of imaging device 28 and data generated during the imaging of the detrusor muscle. Memory 72 may store measurement programs 74 and bladder information 76. Measurement programs 74 may include instructions used by processor 70 to control imaging device 28 to image contractions within the detrusor muscle of the bladder. For example, measurement programs 74 may include instructions on which of electrodes 24 to use to generate electrograms of the contractions of the detrusor muscle, rates at which to sample sensed signals, and any other instructions related to imaging the detrusor muscle. Measurement programs 74 may also include instructions for processor 70 to generate a map of the imaged detrusor muscle and/or instructions on identifying or locating each of the focal points that initiate coordinated contractions in the detrusor muscle.

Bladder information 76 may include data generated during the imaging of the detrusor muscle. Bladder information 76 may include electrogram data received from sensing module 78, locating coordinates of the bladder, a generated map of the detected contractions (e.g., an isochronal map as in FIGS. 2A and 2B or a map of contraction wave propagation), indications of identified focal points in the detrusor muscle, or any other data generated from sensing module 78 or indicative of focal points in the detrusor muscle. Bladder information 76 may also include time and date stamps to indicate when the detrusor muscle was imaged. Although electrogram data is described as being included in bladder information 76, bladder information 76 may include the data associated with any type of imaging technology used to identify focal points in the detrusor muscle.

Although not shown in FIG. 5, imaging device 28 may include a fluid pump or mechanical actuator configured to inflate expanding device 18 that carries electrodes 24. In some examples, a user may manually inflate or expand expanding device 18. Generally, sensing module 78 senses the electrical signals detected by electrodes 24A, 24B, 24C, and 24D (collectively "electrodes 24"). Sensing module 78 may include switches and/or a multiplexer that selects which electrodes are used to sense electrical signals from the detrusor muscle. Electrodes 24 may be configured as bipolar electrodes or unipolar electrodes. In this manner, all of electrodes 24 may be configured to be placed within bladder 14 or at least one of electrodes 24 may be configured as a ground pad placed external to the patient. Processor 70 may control the operation of sensing module 78 as defined by instructions in measurement programs 74. Alternatively, sensing module 78 may include control circuitry to operate independently of control from processor 70.

As described in FIG. 1, electrodes 24 may be disposed on the exterior of balloon 20 and as a part of expandable device 18. Sensor 80 may be a pressure sensor that detects the pressure within balloon 20 as it is expanded to place electrodes 24 in contact within the inner surface of bladder 14. Processor 70 may monitor the pressure output by sensor 80 and compare the pressure to a threshold. Responsive to determining that the pressure exceeds the threshold, processor 70 may provide an alert to the clinician that balloon 20 is sufficiently expanded. In other examples, processor 70 may control a pump that inflates balloon 20 and may automatically terminate inflation in response to determining that the pressure sensed by sensor 80 exceeds the threshold.

Imaging device 28 may be configured to receive inputs from a user. Input devices 82 may include one or more buttons, keypads, touch-sensitive screen, pointing device, or any other input device. Output devices 84 may include one or more lights, a speaker, and a display, such as a liquid crystal (LCD), light-emitting diode (LED), or cathode ray tube (CRT) display. In some examples, the display may be a touch screen. Output devices 84 may thus be configured to output information to a user. Processor 70 may be configured to control input devices 82 and output devices 84. For example, processor 70 may control output device 84 to present a map of identified focal points for the patient's detrusor muscle. In some examples, the combination of input devices 82 and output devices 84 may be referred to as a user interface for imaging device 28.

Although not shown in FIG. 5, imaging device 28 may also include a communication module configured to receive data from another computing device and/or transmit data to another computing device. The communication module may be configured to communicate via wired or wireless communication protocols for direct communication or via a network. Examples of wireless communication techniques that may be employed to facilitate communication between imaging device 28 and another computing device include RF communication according to the 802.11 or Bluetooth specification sets, infrared communication, e.g., according to the IrDA standard, or other standard or proprietary telemetry protocols.

Power source 86 delivers operating power to the components of imaging device 28. Power source 86 may include a battery and a power generation circuit to produce the operating power. In some examples, the battery may be rechargeable to allow extended operation. In other examples, power source 86 may be configured to receive power from an alternating current (AC) outlet.

Figure 6:
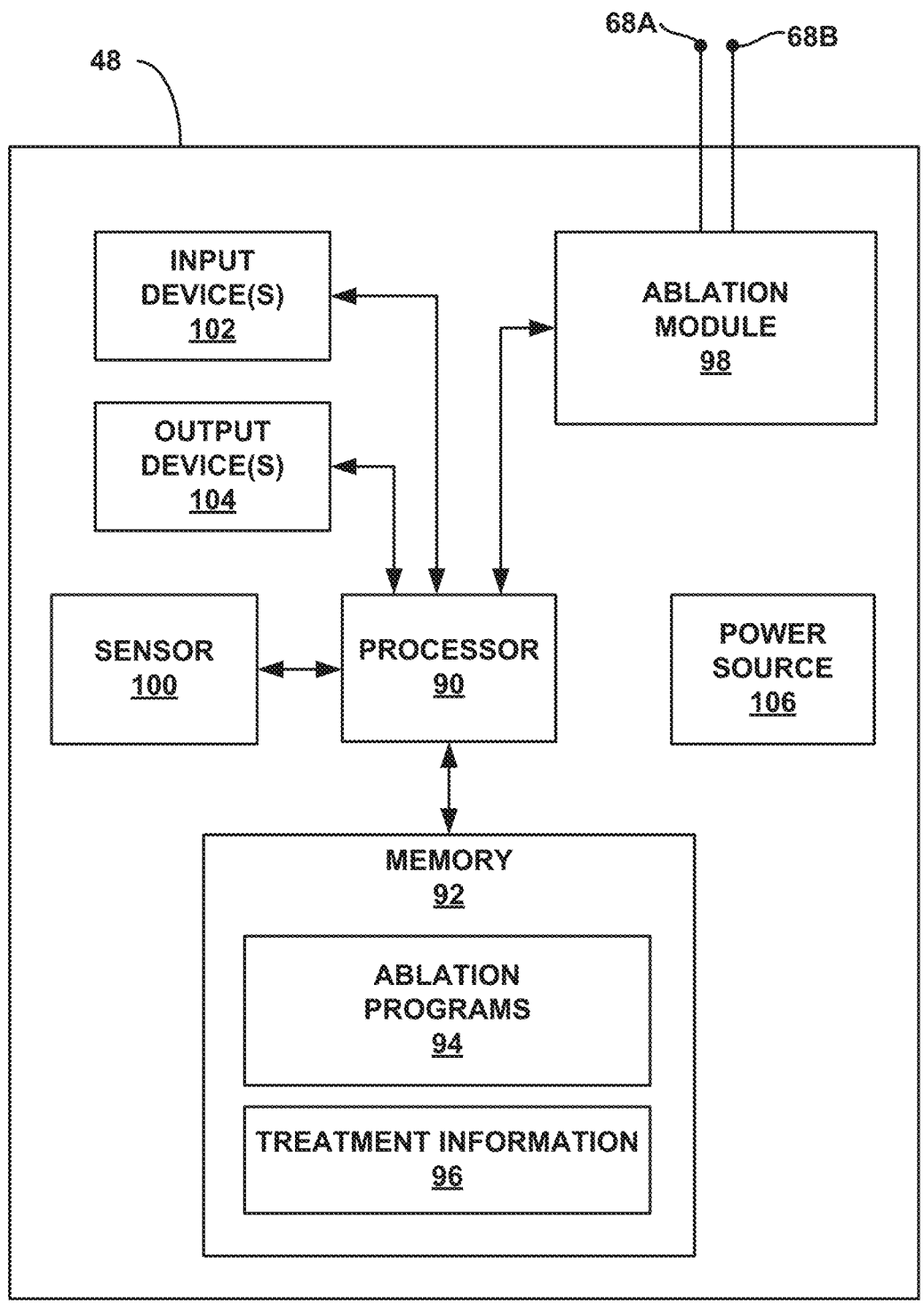
FIG. 6 is a block diagram illustrating an example configuration of an ablation device which may be utilized in the system of FIG. 3 or 4.

FIG. 6 is a block diagram illustrating an example configuration of ablation device 48 which may be utilized in systems 40 and 60 of FIGS. 3 and 4, respectfully. In the example of FIG. 6, ablation device 48 includes processor 90, memory 92, ablation module 98, sensor 100, input devices 102, output devices 104, and power source 106. In other examples, ablation device 48 may include more or fewer components. For example, ablation device 48 may include a telemetry module for wirelessly transmitting data or ablation device 48 may not include sensor 100.

In general, ablation device 48 may comprise any suitable arrangement of hardware, alone or in combination with software and/or firmware, to perform the techniques attributed to ablation device 48 and processor 90 and ablation module 98 of ablation device 48. In various examples, processor 90 of ablation device 48 may include one or more processors, such as one or more microprocessors, digital signal processors (DSPs), application specific integrated circuits (ASICs), field programmable gate arrays (FPGAs), or any other equivalent integrated or discrete logic circuitry, as well as any combinations of such components. Ablation device 48 also, in various examples, may include a memory 92, such as random access memory (RAM), read only memory (ROM), programmable read only memory (PROM), erasable programmable read only memory (EPROM), electronically erasable programmable read only memory (EEPROM), flash memory, comprising executable instructions for causing the one or more processors to perform the actions attributed to them. Moreover, although processor 90 and ablation module 98 are described as separate modules, in some examples, processor 90 and ablation module 98 (or more devices of ablation device 48) are functionally integrated. In some examples, processor 90 and ablation module 98 correspond to individual hardware units, such as ASICs, DSPs, FPGAs, or other hardware units.

Memory 92 stores information such as data for the operation of ablation device 48 and data generated during the targeted ablation of portions of the detrusor muscle corresponding to identified focal points. Memory 92 may store ablation programs 94 and treatment information 96. Ablation programs 94 may include instructions used by processor 90 to control ablation device 48 to ablate tissue, such as portions of the detrusor muscle and/or portions of nerves exterior of the bladder that innervate the detrusor muscle. For example, ablation programs 94 may include instructions for generating an RF signal applied to electrodes 68A and 68B (collectively "electrodes 68") such as ablation parameters. Ablation parameters may include selected electrode configurations, voltage amplitudes, current amplitudes, signal frequency, duty cycles, or any other parameters that define the RF signal. In addition, ablation programs 94 may include thresholds that control the delivery of the RF signal such as temperature thresholds (monitored from a temperature sensor such as sensor 100), time thresholds, impedance thresholds, any other closed-loop or open-loop control mechanisms. Ablation programs 94 may also include algorithms that analyze the mapping of focal points in the detrusor muscle and generate instructions for the clinician that assist the clinician to selectively ablate the portions of the detrusor muscle that correspond to the identified focal points. Ablation programs 94 may additionally include instructions for processor 90 to control input devices 102 to receive user input and output devices 104 to present information to the user. Although ablation programs 94 are described for RF ablation therapy, similar ablation parameters and instructions may be also applicable for controlling different types of ablation therapy such as ultrasound ablation, thermal ablation, mechanical ablation, cryoablation, or any other methods for damaging or removing portions of the detrusor muscle corresponding to identified focal points.

Treatment information 96 may include data generated during the ablation of the detrusor muscle. Treatment information 96 may include times that ablation therapy was delivered, the number of different locations ablated by ablation device 48, the sensed temperatures of impedances from sensor 100, calculated or detected sizes of ablated tissue, or any other information. Processor 90 may, in some examples, present treatment information 96 to the user via output devices 104 and/or transmit treatment information 96 to another computing device via a communication module (not shown in FIG. 6). Treatment information 96 may also include time and date stamps to indicate when the detrusor muscle was ablated, an indication of the patient that received the ablation, and/or an identity of the clinician that performed the ablation. Treatment information 96 may also correlate ablation information to a map of the identified focal points to indicate (e.g., graphically or numerically) which portions of the map were ablated in relation to the focal points. Treatment information 96 may also include any detected errors that occurred during the ablation process.

Generally, ablation module 98 is configured to generate and deliver ablation energy via electrodes 68. In this example of FIG. 6, ablation module 98 may include an RF signal generator that generates an RF signal transmitted to tissue via electrodes 68. The RF signal may be configured to increase the temperature of tissue and cause the desired ablation of that tissue. Processor 90 may control ablation module 98 or ablation module 98 may include separate processing circuitry configured to control the delivery of ablation energy according to ablation programs 94. Ablation module 98 may be configured to deliver bipolar or unipolar ablation and utilize more than two electrodes in other examples. In examples of ablation device 48 where a different ablation technique is used, ablation module 98 may be configured to generate and deliver the appropriate ablation therapy. For example, ablation module 98 may include circuitry configured to module ultrasound transducers for ultrasound ablation or resistively heat elements that provide thermal ablation. In some examples, ablation module 98 may include a pump and conduit that deliver conductive fluid to help distribute RF energy to the tissue. Alternatively, ablation module 98 may include a pump and conduit configured to deliver chemicals that ablate tissue or cryogenic fluid that freeze tissue via one or more catheters terminating at a targeted tissue location.

Sensor 100 may be a temperature sensor that detects the temperature of tissue adjacent to electrodes 68 during the delivery of RF energy. Sensor 100 may receive a signal from a thermocouple, thermistor, or other probe disposed on the catheter also carrying electrodes 68. Processor 90 may monitor the temperature output by sensor 100 and compare the temperature to a threshold. Responsive to determining that the temperature exceeds the threshold, processor 90 may automatically terminate delivery of the RF energy and/or output an alert to be presented to the user via output devices 104. In other examples, sensor 100 be an impedance sensor may monitor changes in impedance that indicate ablation progress or any other type of sensor appropriate for the type of ablation being delivered by ablation device 48.

Ablation device 48 may be configured to receive inputs from a user. Input devices 102 may include one or more buttons, keypads, touch-sensitive screen, pointing device, or any other input device. Output devices 104 may include one or more lights, a speaker, and a display, such as a liquid crystal (LCD), light-emitting diode (LED), or cathode ray tube (CRT) display. In some examples the display may be a touch screen. Output devices 104 may thus be configured to output information (e.g., the status of ablation therapy and/or treatment information 96) to a user. Processor 90 may be configured to control input devices 102 and output devices 104. For example, processor 90 may control output device 104 to present a status of current RF energy delivery and/or a temperature of the ablated tissue sensed from sensor 100. Processor 90 may also control output devices 104 to present the previously generated map of identified focal points and update the map as focal points are ablated. In some examples, the combination of input devices 102 and output devices 104 may be referred to as a user interface for ablation device 48.

Although not shown in FIG. 6, ablation device 48 may also include a communication module configured to receive data from another computing device and/or transmit data to another computing device. The communication module may be configured to communicate via wired or wireless communication protocols for direct communication or via a network. Examples of wireless communication techniques that may be employed to facilitate communication between ablation device 48 and another computing device include RF communication according to the 802.11 or Bluetooth specification sets, infrared communication, e.g., according to the IrDA standard, or other standard or proprietary telemetry protocols.

Power source 106 delivers operating power to the components of ablation device 48. Power source 106 may include a battery and a power generation circuit to produce the operating power. In some examples, the battery may be rechargeable to allow extended operation. In other examples, power source 106 may be configured to receive power from an alternating current (AC) outlet.

Figure 7:
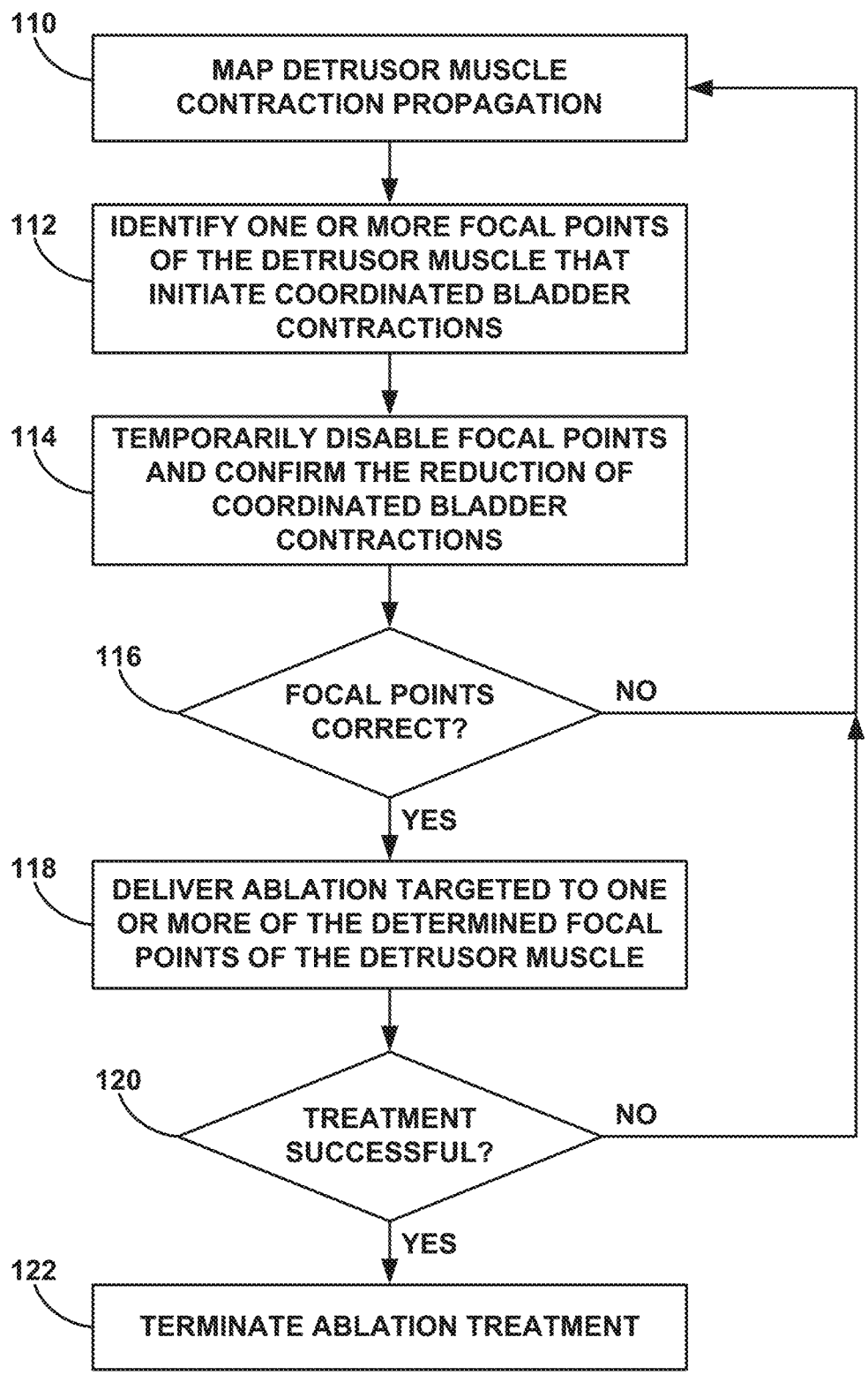
FIG. 7 is a flow diagram that illustrates an example technique for identifying focal points that initiate coordinated bladder contractions and ablating portions of detrusor muscle corresponding to locations of the identified focal points.

FIG. 7 is a flow diagram that illustrates an example technique for identifying focal points that initiate coordinated bladder contractions and ablating portions of detrusor muscle corresponding to locations of the identified focal points. As described in FIG. 7, processor 70 of imaging device 28 may be used to image detrusor muscle 16 of patient 12 and processor 90 of ablation device 48 may be used to selectively ablate portions of detrusor muscle 16. However, in other examples, a single device may incorporate the functionality of both imaging device 28 and ablation device 48. Although the example of FIG. 7 is directed to focal points within detrusor muscle 16, focal points may be identified, and ablated, in any bladder tissue.

Imaging device 28 may initially image and map contraction propagation of detrusor muscle 16 in patient 12 (110). As discussed herein, imaging detrusor muscle 16 may include monitoring detrusor muscle contractions and where the contractions are initiated. Imaging device 28 may then map the contraction propagation based on the imaging data generated by imaging device 28. Imaging device 28 may then identify one or more focal points of detrusor muscle 16 that initiate coordinated bladder contractions (112). Initiation points that are only involved with uncoordinated contractions are not identified as focal points. In other words, imaging device 28 identifies focal points in detrusor muscle 16 when the contractions are determined to be coordinated from locations in detrusor muscle 16. In other examples, a clinician or technician may identify one or more of the focal points based on the mapping of contraction propagation within detrusor muscle 16.

Once the focal points are identified, the clinician may confirm that the identical focal points actually initiate the coordinated contractions. The clinician may temporarily disable the identified focal points in detrusor muscle 16 and confirm that the temporary disability of the focal points reduces or eliminates the coordinated bladder contractions (114). The clinician may temporarily disable focal points by injecting or applying an analgesic (e.g., Botox® or lidocaine) to the location of bladder 14 or detrusor muscle 16 corresponding to the identified focal points. If the coordinated contractions may remain or are not reduced to a satisfactory level, the clinician may determine that not all of the focal points are correct ("NO" branch of block 116) and re-map contractions (110).

If the focal points are correct because contractions are reduced to the satisfactory level ("YES" branch of block 116), the clinician may proceed to use ablation device 48 to deliver ablation targeted to one or more of the determined focal points of detrusor muscle 16 (118). As described herein, the targeted ablation may be directed to the portions of detrusor muscle 16 (and/or nerves that innervate these portions of detrusor muscle 16) corresponding to the identified focal points instead of portions of detrusor muscle 16 corresponding to areas not identified as focal points. In other words, the targeted ablation may limit ablated tissue to those locations in which focal points are determined to exists. In some examples, a single ablation event (e.g., a continuous delivery of ablation energy) may be sufficient to ablate the targeted tissue. However, in some examples, the clinician may deliver a series of ablation events to treat each of the one or more focal points. In addition, in some examples, the clinician may perform imaging of the focal points at one or more times between at least some or all of the series of ablation events. This imaging may provide feedback to determine when the targeted ablation has been successful and the series of ablation events can be stopped.

Ablation device 48 may be configured to deliver, as controlled by processor 90, different types of ablation (e.g., RF ablation, thermal ablation, mechanical ablation, ultrasound ablation, or cryoablation). If the clinician determines that the treatment has not been successful, e.g., coordinated contractions and overactive bladder remain, ("NO" branch of block 120), the clinician may again instruct imaging device 28 to map the focal points (110). This subsequent mapping of focal points may be performed during the same clinic visit or at another later clinic visit for the patient. If the clinician determines that the treatment has been successful because coordinated contractions have been reduced or eliminated ("YES" branch of block 120), the clinician may terminate the ablation treatment (122).

Although the clinician has been described as performing some of the processes of FIG. 7 with the aid of imaging device 28 and ablation device 48, a completely automated process may be conducted by imaging device 28 and ablation device 48. In other words, processor 70 and/or processor 90 may control the mapping of detrusor muscle 16 and the delivery of ablation to eliminate the identified focal points. Such an automated system may be a combined system of imaging device 28 and ablation device 48 such that the clinician only has to insert a single multi-functional device within bladder 14. The single multi-functional device may include imaging sensors and ablation delivery mechanisms.

Figure 8:
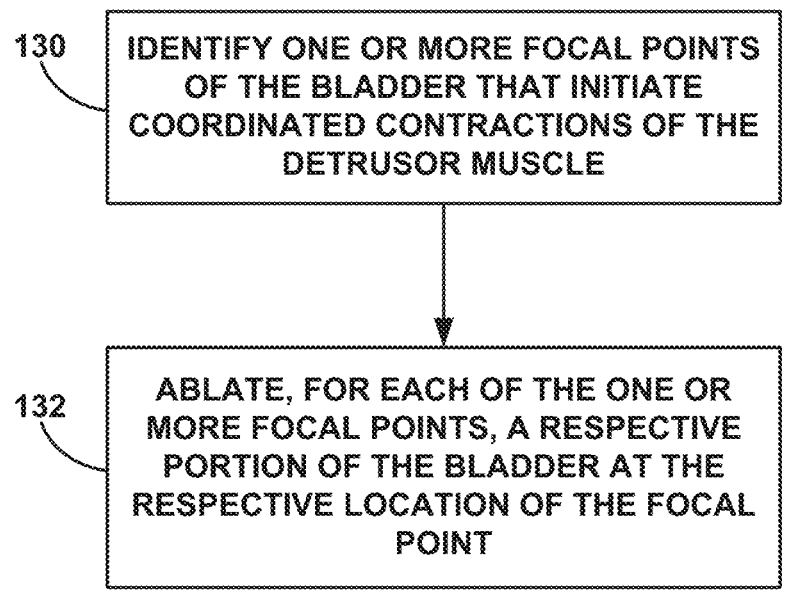
FIG. 8 is a flow diagram that illustrates an example technique for identifying focal points that initiate coordinated bladder contractions and ablating portions of bladder tissue corresponding to locations of the identified focal points.

FIG. 8 is a flow diagram that illustrates an example technique for identifying focal points that initiate coordinated bladder contractions and ablating portions of bladder tissue corresponding to locations of the identified focal points. As described in FIG. 8, processor 70 of imaging device 28 may be used to image bladder tissue of patient 12 and processor 90 of ablation device 48 may be used to selectively ablate portions of bladder tissue. However, in other examples, a single device may incorporate the functionality of both imaging device 28 and ablation device 48.

Imaging device 28 may identify, or assist in the identification of, one or more focal points of bladder tissue that initiate coordinated contractions of detrusor muscle 16 of bladder 14 (130). Initiation points that are only involved with uncoordinated contractions are not identified as focal points in bladder tissue. In other words, imaging device 28 identifies focal points in bladder tissue when the contractions of detrusor muscle 16 are determined to be coordinated from locations in the bladder tissue of bladder 14. As discussed herein, bladder tissue can include urothelium, detrusor muscle 16, or nerves controlling at least a portion of detrusor muscle 16.

Ablation device 48 may then ablate, for each of the one or more focal points, a respective portion of the bladder tissue at the respective location of the focal point (132). The targeted ablation may include the focal point of the bladder tissue, such as portions of urothelium, detrusor muscle 16, and/or nerves that control detrusor muscle 16. Ablation device 48 may be automated (e.g., as part of imaging device 28) or used by a user (e.g., a clinician or technician) to ablate the targeted portions of bladder tissue. In some examples, a single ablation event (e.g., a continuous delivery of ablation energy) may be sufficient to ablate the targeted tissue at a single location (e.g., at each focal point). However, in some examples, the clinician may deliver a series of ablation events to treat each of the one or more targeted locations to receive ablation. In addition, in some examples, the clinician may perform imaging of the focal points between at least some of the series of ablation events. This imaging may provide feedback to determine when the targeted ablation has been successful and the series of ablation events can be stopped.

This disclosure describes various techniques. In one example, a method for treating bladder dysfunction in a patient includes identifying one or more focal points at respective locations of bladder tissue of a bladder of the patient, the one or more focal points initiating coordinated contractions of a detrusor muscle in the bladder and ablating, for each of the one or more focal points, a respective portion of the bladder tissue at the respective location of the focal point.

In another example, a method for treating bladder dysfunction in a patient includes selecting first portion of bladder tissue in a bladder of the patient, wherein the first portion corresponds to a first focal point of a plurality of focal points, each focal point of the plurality of focal points being identified as initiating coordinated contractions of a detrusor muscle, ablating the first portion of the bladder tissue, selecting a second portion of the bladder tissue corresponding to a second focal point of the plurality of focal points, and ablating the second portion of the bladder tissue.

In another example, a method for treat bladder dysfunction in a patient imaging propagation of contractions in a detrusor muscle in a bladder of the patient, mapping, based on the imaged propagation of contractions, one or more focal points at respective locations of bladder tissue, the one or more focal points initiating coordinated contractions of the detrusor muscle, targeting, for each of the one or more mapped focal points of the bladder tissue, respective portions of the bladder tissue, and not targeting portions of the bladder tissue corresponding to non-focal points of the bladder tissue, and ablating, for each of the one or more focal points, the targeted respective portion of the bladder tissue at the respective location of the focal point to reduce the coordinated contractions of the detrusor muscle and overactive bladder symptoms.

The techniques of this disclosure may be implemented in a wide variety of computing devices, medical devices, or any combination thereof. Any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The disclosure contemplates computer-readable storage media comprising instructions to cause a processor to perform any of the functions and techniques described herein. The computer-readable storage media may take the example form of any volatile, non-volatile, magnetic, optical, or electrical media, such as a RAM, ROM, NVRAM, EEPROM, or flash memory that is tangible. The computer-readable storage media may be referred to as non-transitory. A server, client computing device, or any other computing device may also contain a more portable removable memory type to enable easy data transfer or offline data analysis.

The techniques described in this disclosure, including those attributed to imaging device 28, ablation device 48, and various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, remote servers, remote client devices, or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in an article of manufacture including a computer-readable storage medium encoded with instructions. Instructions embedded or encoded in an article of manufacture including a computer-readable storage medium encoded, may cause one or more programmable processors, or other processors, to implement one or more of the techniques described herein, such as when instructions included or encoded in the computer-readable storage medium are executed by the one or more processors. Example computer-readable storage media may include random access memory (RAM), read only memory (ROM), programmable read only memory (PROM), erasable programmable read only memory (EPROM), electronically erasable programmable read only memory (EEPROM), flash memory, a hard disk, a compact disc ROM (CD-ROM), a floppy disk, a cassette, magnetic media, optical media, or any other computer readable storage devices or tangible computer readable media. The computer-readable storage medium may also be referred to as storage devices.

In some examples, a computer-readable storage medium comprises non-transitory medium. The term "non-transitory" may indicate that the storage medium is not embodied in a carrier wave or a propagated signal. In certain examples, a non-transitory storage medium may store data that can, over time, change (e.g., in RAM or cache).

Various examples have been described herein. Any combination of the described operations or functions is contemplated. These and other examples are within the scope of the following claims.

What is claimed is:

1. A method for treating bladder dysfunction in a patient, the method comprising:
    identifying one or more focal points at respective locations of bladder tissue of a bladder of the patient, the one or more focal points initiating coordinated contractions of a detrusor muscle in the bladder;
    injecting a substance into at least one respective portion of the bladder tissue at the respective locations of the one or more focal points, the substance configured to temporarily disable initiation of contractions;
    confirming that the substance reduces coordinated contractions of the detrusor muscle; and
    based on the confirmation, ablating, for each of the one or more focal points, the respective portion of the bladder tissue at the respective location of the focal point.

2. The method of claim 1, wherein identifying the one or more focal points comprises:
    imaging propagation of contractions in the detrusor muscle; and
    mapping, based on the imaged propagation of contractions, the one or more focal points at the respective locations of the bladder tissue.

3. The method of claim 2, wherein imaging the propagation of contractions comprises at least one of optically determining the propagation of contractions, obtaining electrogram information for the propagation of contractions, optically determining calcium movement for the propagation of contractions, magnetic resonance imaging the propagation of contractions, or ultrasound imaging of the propagation of contractions.

4. The method of claim 1, further comprising inserting an ablation instrument into the bladder via a urethra, wherein ablating the respective portions of the bladder tissue comprises directing the ablation to an inner surface of the bladder via the ablation instrument located within the bladder.

5. The method of claim 1, wherein ablating a respective portion of the bladder tissue comprises ablating a portion of at least one of a urothelium or the detrusor muscle.

6. The method of claim 1, wherein ablating a respective portion of the bladder tissue comprises ablating a portion of a nerve residing external to the detrusor muscle, wherein the nerve controls at least a portion of the detrusor muscle associated with at least one of the one or more focal points.

7. The method of claim 1, wherein ablating the respective portions of the bladder tissue comprises ablating the respective portions of the detrusor muscle associated with the focal points and not ablating portions associated with the non-focal points of the detrusor muscle.

8. The method of claim 1, wherein ablating the respective portions of the bladder tissue comprises ablating the respective portions of the bladder tissue via at least one of chemical ablation, radio frequency ablation, ultrasound ablation, mechanical ablation, heat ablation, or cyroablation.

9. The method of claim 1, wherein the one or more focal points are a subset of a plurality of focal points that initiate respective coordinated contractions of the detrusor muscle.

10. The method of claim 1, wherein coordinated contractions of the detrusor muscle promote an overactive bladder condition for the patient, and wherein ablating the respective portions of the bladder reduces the coordinated contractions of the detrusor muscle to treat the overactive bladder condition.

11. The method of claim 1, wherein ablating the respective portions of the bladder tissue comprises delivering targeted ablation to the respective portions of the bladder tissue to reduce the coordinated contractions of the detrusor muscle and overactive bladder symptoms.

12. The method of claim 1, wherein the bladder tissue comprises one or more of the detrusor muscle, a urothelium, and nerves that control the detrusor muscle.

13. A method for treating bladder dysfunction in a patient, the method comprising:
    selecting a first portion of bladder tissue in a bladder of the patient, wherein the first portion corresponds to a first focal point of a plurality of focal points, each focal point of the plurality of focal points being identified as initiating coordinated contractions of a detrusor muscle;

injecting a substance into the first portion of the bladder tissue, the substance configured to temporarily disable initiation of contractions;

confirming that the substance reduces coordinated contractions of the detrusor muscle;

based on the confirmation, ablating the first portion of the bladder tissue;

selecting a second portion of the bladder tissue corresponding to a second focal point of the plurality of focal points; and ablating the second portion of the bladder tissue.

14. The method of claim 13, further comprising identifying the plurality of focal points at respective locations of the bladder tissue, each focal point of the plurality of focal points initiating coordinated contractions of the detrusor muscle.

15. The method of claim 14, wherein identifying the plurality of focal points comprises:

imaging propagation of contractions in the detrusor muscle; and mapping, based on the imaged propagation of contractions, the plurality of focal points at the respective locations of the bladder tissue.

16. The method of claim 13, further comprising inserting an ablation instrument into the bladder via a urethra, wherein ablating the first and second portions of the bladder tissue comprises directing the ablation to respective inner surfaces of the bladder via the ablation instrument located within the bladder.

17. The method of claim 13, wherein selecting the first and second portions of the bladder tissue comprises selecting the first and second portions of the bladder tissue and not selecting portions of the bladder tissue corresponding to non-focal points of the bladder tissue, non-focal points being unidentified as initiating coordinated contractions of the detrusor muscle.

18. The method of claim 13, wherein ablating the first and second portions of the bladder tissue comprises ablating the respective portions of the bladder tissue via at least one of chemical ablation, radio frequency ablation, ultrasound ablation, mechanical ablation, heat ablation, or cyroablation.

* * * * *